United States Patent [19]

Sleister et al.

[11] Patent Number: 5,522,831
[45] Date of Patent: Jun. 4, 1996

[54] INCISING TROCAR AND CANNULA ASSEMBLY

[75] Inventors: Dennis R. Sleister, 11 Briarbrook Dr., East Greenwich, R.I. 02818; John G. Mathews, Providence, R.I.

[73] Assignee: Dennis R. Sleister, East Greenwich, R.I.

[21] Appl. No.: 258,780

[22] Filed: Jun. 13, 1994

[51] Int. Cl.$^6$ ..................................... A61M 5/20
[52] U.S. Cl. ...................... 606/182; 604/157; 128/751
[58] Field of Search .................. 606/182, 167, 606/181, 184–185; 128/751; 604/164, 264

[56] References Cited

U.S. PATENT DOCUMENTS

| | | | |
|---|---|---|---|
| 1,380,447 | 6/1921 | Wescott . | |
| 4,490,136 | 12/1984 | Ekbladh et al. | 604/272 X |
| 4,535,773 | 8/1985 | Yoon | 604/169 X |
| 4,601,710 | 7/1986 | Moll | 604/165 |
| 4,917,668 | 4/1990 | Haindl | 604/167 |
| 5,009,643 | 4/1991 | Reich et al. | 606/185 X |
| 5,030,206 | 7/1991 | Lander | 606/185 X |
| 5,092,857 | 3/1992 | Fleischhacker | 604/167 X |
| 5,104,382 | 4/1992 | Brinkerhoff et al. | 604/165 |
| 5,104,383 | 4/1992 | Shichman | 604/167 |
| 5,116,353 | 5/1992 | Green | 606/184 |
| 5,127,626 | 7/1992 | Hilal et al. | 604/167 X |
| 5,129,858 | 7/1992 | Komori et al. | 454/155 |
| 5,147,316 | 9/1992 | Castillenti | 606/185 X |
| 5,152,754 | 10/1992 | Plyley et al. | 604/164 |
| 5,158,552 | 10/1992 | Borgia et al. | 604/165 |
| 5,176,651 | 1/1993 | Allgood et al. | 604/167 |
| 5,197,955 | 3/1993 | Stevens et al. | 604/167 |
| 5,209,737 | 5/1993 | Ritchart et al. | 606/167 |
| 5,215,526 | 1/1993 | Deniega et al. | 606/185 X |
| 5,217,441 | 6/1993 | Shichman | 606/185 X |
| 5,217,451 | 6/1993 | Freitas | 606/1 |
| 5,304,193 | 4/1994 | Zhadanov | 606/185 X |
| 5,306,282 | 4/1994 | Muller | 606/167 X |
| 5,312,354 | 5/1994 | Allen et al. | 128/754 X |
| 5,314,417 | 5/1994 | Stephen et al. | 606/167 X |

Primary Examiner—Stephen C. Pellegrino
Assistant Examiner—Nancy Mulcare
Attorney, Agent, or Firm—Aquilino & Welsh

[57] ABSTRACT

An incising trocar and cannula instrument for incising the walls of a body cavity to facilitate inserting the cannula through the wall into the cavity including a trigger operated incising blade and means for driving the blade through body tissue; and, a cannula having a sealing assembly for sealing the instrument during the incising procedure and thereafter when the trocar is removed.

10 Claims, 4 Drawing Sheets

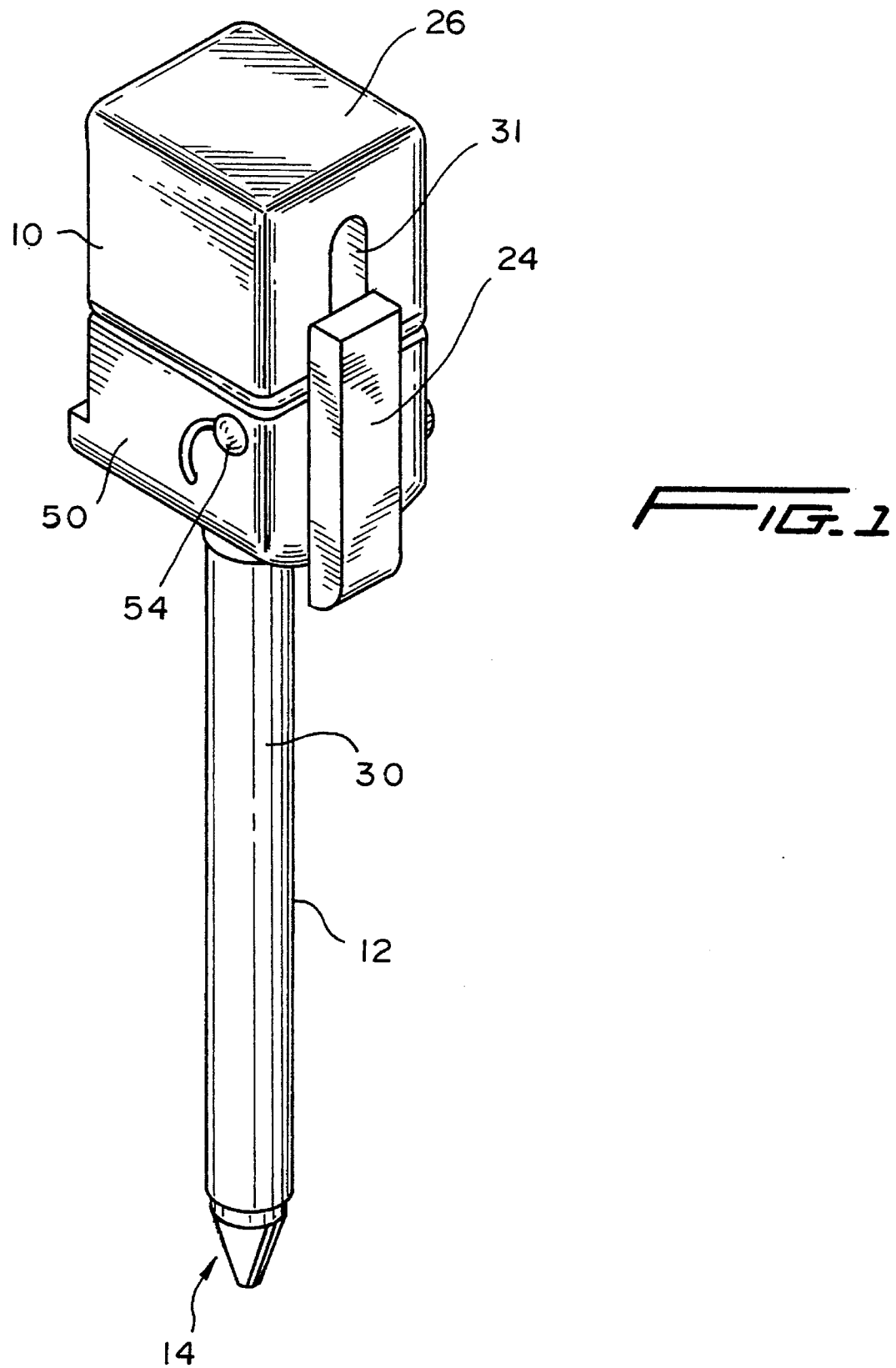

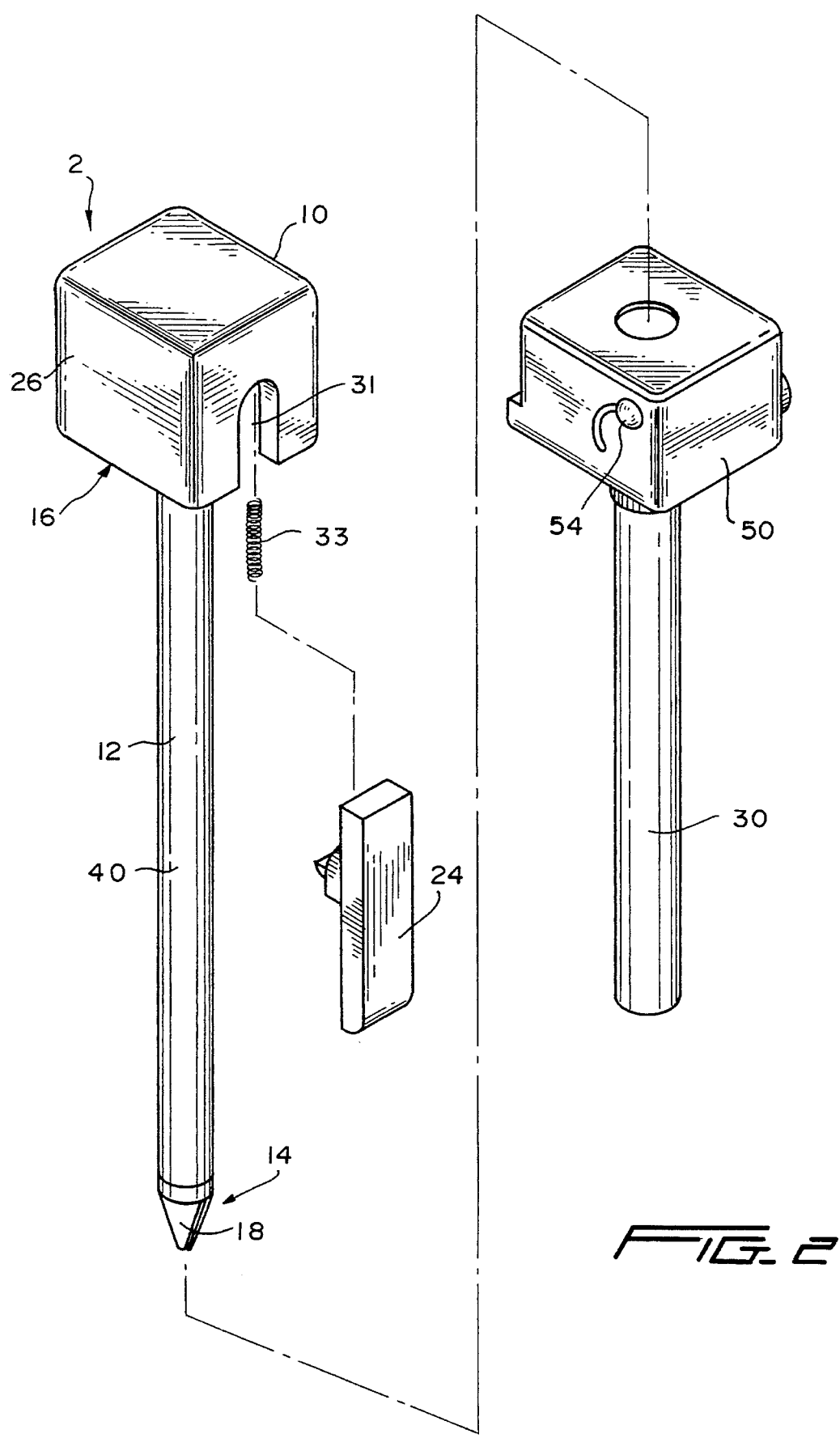

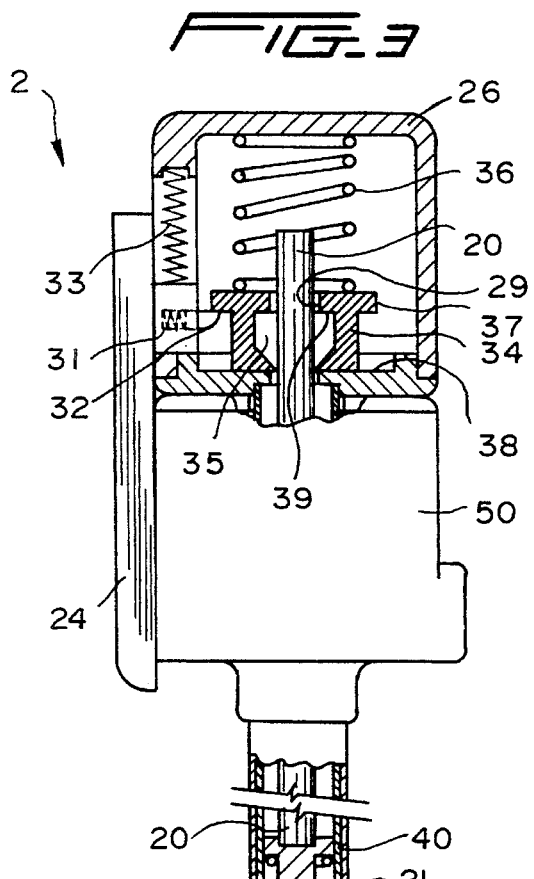
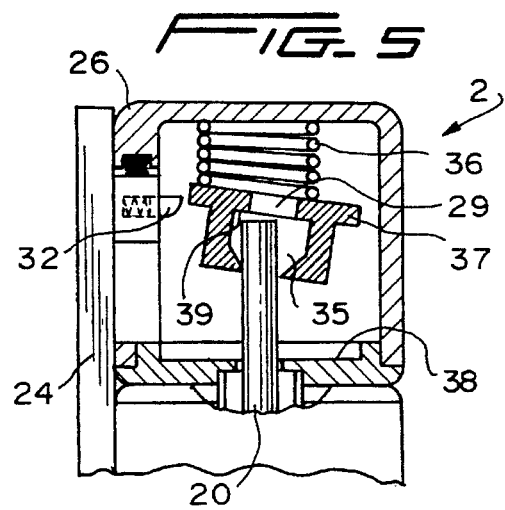
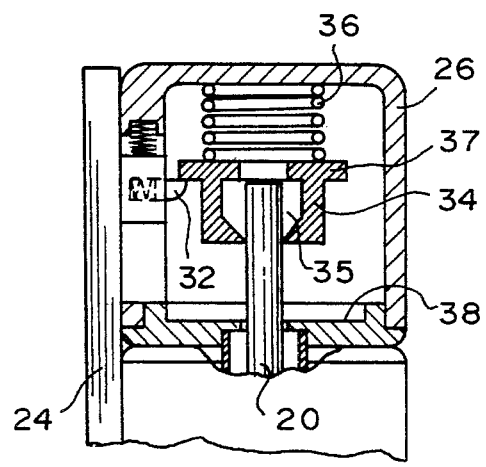
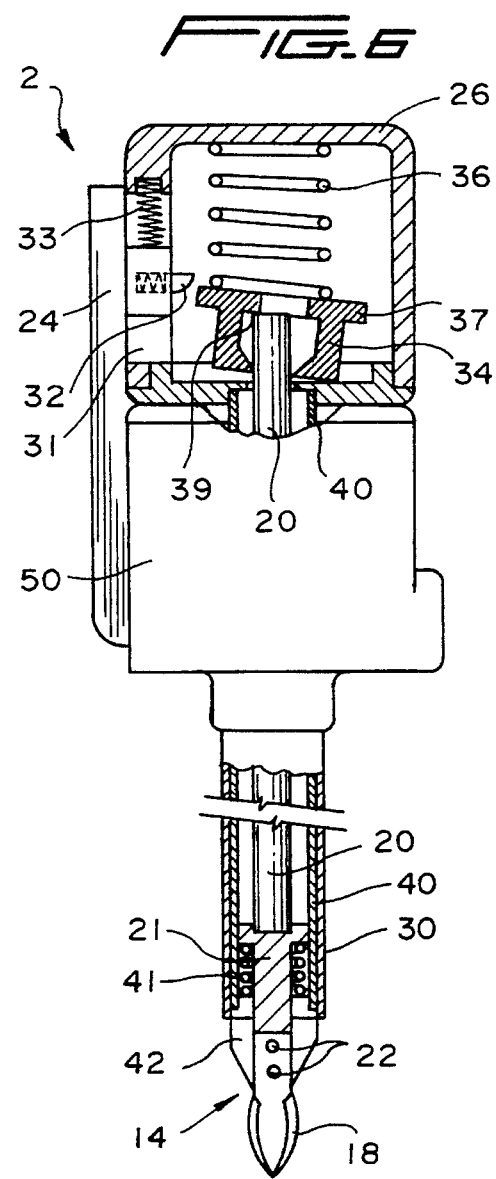

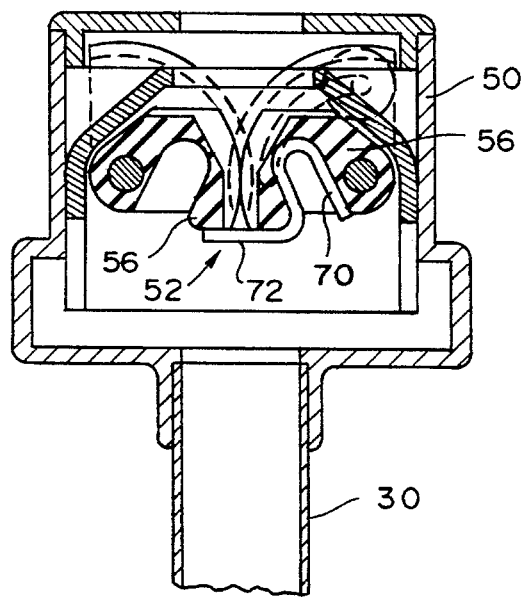
FIG_7
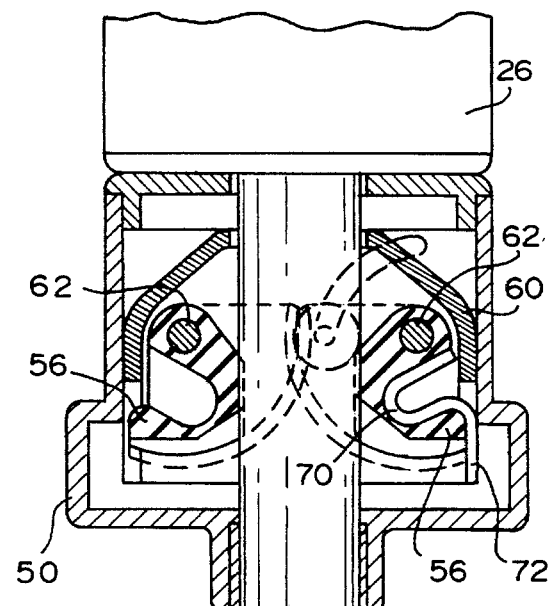
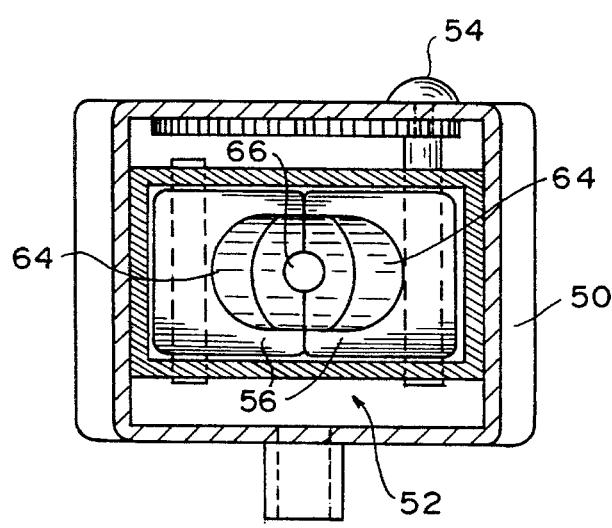
FIG_8
FIG_9

INCISING TROCAR AND CANNULA ASSEMBLY

BACKGROUND OF THE INVENTION

1. Field of the Invention

The present invention relates to medical instruments and, in particular, to a trocar/cannula combination with built-in safety mechanisms which maintain an air-tight seal when the surgeon passes surgical instruments through it.

Trocars are typically sharp pointed surgical instruments used to puncture a body cavity and are designed to be used with a cannula in the form of an outer sleeve which after the trocar is removed, permits the insertion of surgical instruments to allow a surgeon to perform various procedures without the necessity of leaving the body cavity open. Thus, the trocar creates a passageway through a body wall in order that the surgeon may gain access to an interior portion of the body. Once the body cavity has been punctured by the trocar, the sharp trocar is removed from the cannula thereby leaving the cannula extending into the body cavity. Surgical procedures may then be performed through the cannula with accessory instrumentation such as laparoscopes, endoscopes, dissectors, graspers and similar type instruments.

Trocars provide a means for penetrating tissue and muscle. The prior art trocars were large steel shafts with a sharpened point. However, when inserting the trocar, a surgeon must exert considerable force on the proximal end so that the sharpened tip would provide a cutting and separating action at the same time. The force required to penetrate the body wall is related to the resistance of the tissue and muscle as well as the size and sharpness of the trocar tip. Often forcing the trocar through the body wall resulted in the trocar plunging through the body wall and injuring body organs or other tissue or vessels underneath.

2. Description of the Prior Art

Prior art trocars have been designed which provide a safety shield which plunges forward after penetration, covering the trocar tip and protecting the patient. These designs use a safety cover which is projected forward to cover the trocar's distal end or provide a mechanism for retracting the cutting tip while leaving the safety shield extended.

One example of a safety trocar is shown in U.S. Pat. No. 4,535,773 to Yoon. The trocar in this invention provides a safety shield which is spring loaded and which extends forward into the body cavity surrounding the point of the obturator when resistance of the tissue is removed. A trocar of this type requires the incision formed by the obturator to extend to a considerable diameter before the resistance of the tissue pressure has been sufficiently decreased to allow the safety shield to spring forward.

Another safety trocar of interest is shown in the patent to Moll (U.S. Pat. No. 4,601,710) which describes a trocar assembly consisting of two subassemblies, a sharp tipped trocar and a spring loaded tubular safety shield and a cannula subassembly. Initially the safety shield covers the trocar tip and exertion of pressure against the skin with the trocar causes the shield to be pushed rearwardly to expose the cutting tip. After the skin is penetrated through the wall, the force against the front end of the shield ceases and the shield automatically moves back to its distally extended position thereby protecting internal tissue from the sharp piercing tip.

The patent to Green (U.S. Pat. No. 5,116,353) describes a safety trocar whereby the cutting tip is withdrawn into a cannula in response to a counterforce being removed from the cutting tip when the tip enters a body cavity. The cutting tip is automatically withdrawn into the cannula under the force of a spring by means of a release mechanism which is actuated when resistance against penetration is lowered.

Still another patent of interest is to Deniega et al. (U.S. Pat. No. 5,215,526) which discloses a safety trocar including a spring loaded shield which covers the cutting tip of the obturator once it penetrates tissue. The distal end of the shield is hemispheric and contains a slot which conforms to the geometry of the cutting tip. The trocar also includes a valve at the proximal end to seal the end of the tube to prevent evacuation of gases from the body cavity.

In addition to the above, a number of prior art patents recognize the need for providing a seal at the proximal end of the trocar cannula structure to prevent venting of the body cavity. Another patent to Green (U.S. Pat. No. 5,129,885) provides a safety locking device for assuring proper matching relationship between a surgical instrument and a trocar guide tube or cannula housing.

The Shichman patent (U.S. Pat. No. 5,104,383) relates to a trocar seal for use with a cannula assembly for use with a variety of different sized instruments. The seal uses a stabilizer plate to limit the eccentric movement of the instrument to prevent inadvertent release of the seal.

The Stevens et al. patent (U.S. Pat. No. 5,197,955) relates to a trocar assembly which includes an improved seal to accommodate instruments having a wide range of diameters. A universal seal member is hourglass shaped and includes converging and diverging side walls forming a constricted center bore therebetween. Means are provided to increase or decrease the inner diameter of the center bore portion of the seal member to accommodate the various sized instruments.

The Ritchart et al. patent (U.S. Pat. No. 5,209,737) discloses a septum seal for a trocar assembly including an elastomeric septum disposed in a center channel. An assembly of levers pivot outwardly to expand or contract the seal to change the orifice opening to accommodate various sized instruments.

The Haindl patent (U.S. Pat. No. 4,917,668) discloses a valve for a cannula using a slotted valve body biased in a closed position by a metal spring.

The patent to Hilal et al. (U.S. Pat. No. 5,127,626) relates to an apparatus for sealing around a shaft including an elastomeric sealing body in a housing, a clamp and biasing arrangement to compress the sealing body into a sealed position.

Other patents of interest relating to trocars include, but are not limited to, the patent to Wescott (U.S. Pat. No. 1,380,447), Ekbladh et al. (U.S. Pat. No. 4,490,136), Reich et al. (U.S. Pat. No. 5,009,643), Lander (U.S. Pat. No. 5,030,206), Fleischhacker (U.S. Pat. No. 5,092,857), Brinkerhoff et al. (U.S. Pat. No. 5,104,382), Castillenti (U.S. Pat. No. 5,147,316), Plyley et al. (U.S. Pat. No. 5,152,754), Borgia et al. (U.S. Pat. No. 5,158,552), Allgood et al. (U.S. Pat. No. 5,176,651), Shickman et al. (U.S. Pat. No. 5,217,441) and Freitas (U.S. Pat. No. 5,217,451).

SUMMARY OF THE INVENTION

The prior art trocar/cannula structures use mechanisms which basically work by either projecting a safety cover forward to cover the trocar's distal end or by retracting the cutting tip while leaving the safety shield extended. The trocar of the present invention approaches the problem differently by minimizing the amount of force necessary to penetrate the body wall while providing the surgeon tactile feedback and control over the insertion. This is accomplished by making the trocar of the present invention function closer to an instrument a surgeon is more familiar with. A scalpel is a commonly used surgical instrument used to enter a surgical site during a laparotomy. Thus, the present invention has been designed with a scalpel type incising blade rather than a pyramidal or triangular shaped tip, as with the prior art. The trocar of the present invention consists of an obturator, an incising blade, a drive shaft, a trocar housing which provides a hand grip and a drive mechanism with a trigger. The incising blade is a special scalpel blade made of surgical steel fastened to the drive shaft which runs from the proximal end of the trocar to the distal end. The drive shaft communicates directly with the drive mechanism which may have a variety of different configurations. The drive mechanism converts light finger pressure exerted by the surgeon on the trigger into forward motion of the drive shaft and blade. Pulling the trigger forces the incising blade forward and extends it past the end of the obturator. At the end of the trigger pull, the trigger recoils rapidly and the incising blade retracts back into the obturator. The surgeon receives tactile feedback from the trigger to discern when to trigger the advance of the incising blade.

The trocar differs from other mechanical trocars by separating the cutting action from the penetrating action. In use, the surgeon pulls the trigger when resistance against the distal end indicates an incising action is required. This is similar to using a scalpel to make multiple passes to cut through different planes of tissue. Between trigger activations, pressure is extended on the trocar's proximal end. The distal end of the obturator is shaped to optimize separation of tissue and muscle. In a laparoscopy procedure, when the tenacious peritoneum layer is reached, the surgeon can sense the increased resistance. One or more triggering actions cuts an incision the length of the trocar's diameter. Since this incision must be stretched further to the full diameter of the trocar and cannula, there is ample time for the incising blade to retract before the full penetration into the cavity is accomplished. When penetration is obtained, the trocar is removed and the cannula is left in place.

The cannula function is to provide an airtight passageway into the surgical site which is accessible only because the cavity is distended by gas insufflation. The surgeon uses the passage to insert an endoscope for viewing. Additional cannula can be placed to allow passage of surgical instruments and removal of tissue. The cannula must keep the higher pressure gas on its distal side from leaking out when surgical instruments of various sizes are used in it. To accomplish this seal, the cannula consists of a housing incorporating a universal dynamic seal which automatically adjusts to the diameter of the instrument while providing an absolute seal when there is no instrument in the channel. In addition, a release button allows partial or full opening of the cannula to permit desufflation, venting of the inner cavity gases, or removal of tissue.

The cannula seal includes two parallel rotating multi-diameter seal members mounted perpendicular to the channel and across the shorter access of the housing. A roller bar for each member has a tapered groove, a linkage mechanism to synchronize the position of the bars such that the radius of the facing hemispheres are identical and a spring to maintain a smooth and sufficient load on the roller bars. A lever connecting the linkage mechanism to the release button outside of the housing allows opening of the seal. A secondary seal is provided below the self-adjusting seal to close the channel from the minimum diameter of the roller bars to zero, thereby providing an air-type compartment below the seal. An optional egress port may be provided to mate with common tubing or valves. A cannula sleeve of the appropriate diameter may be used as well as an anchoring mechanism to hold the cannula in place.

When a trocar is inserted into the instrument, the seal is opening fully. Upon removal of the trocar, the seal closes and the cannula is anchored in place. When an instrument is passed through the cannula, the surgeon merely inserts the distal end of the instrument into the proximal opening of the cannula housing and presses it through the seal. As the seal opens, the secondary seal opens ahead of the instruments. After the instrument is advanced, the seal is closed around it by counterpressure which may be spring induced. The tightness of the fit and the friction coefficient of the seal contacting the surface is optimized to permit leak free, slightly resistant movement of the instrument. The surface of the secondary seal is shaped to permit easy instrument movement over it. The distal surface of the tapered roller bar has an opening groove to allow removal of hooked instruments whose trailing distal end is narrower than the portion of the instrument in the seal. In these instances, the trailing protrusion contacts the opening groove and opens the seal. The cannula sleeve itself may consist of various materials including medical grade elastomers, composite material, multi-component conductive materials and metals.

Among the objects of the present invention is the provision of a trocar which minimizes the force necessary to penetrate a body cavity by separating the force or action for cutting or incising tissue from the greater force necessary to penetrate the body wall by separating the tissue and muscles.

Another object of the present invention is to provide a trocar which accomplishes the incising requirements using a scalpel type blade integrally connected to the drive shaft.

Still another object is the provision of a trocar which incorporates a fixed safety shield in the form of an obturator, including an obturator shaft and obturator tip to optimize penetration and separation of the body wall while minimizing risk of damage to underlying tissue structures.

Another object of the present invention is the provision of a trocar which incorporates a low pressure finger driven drive mechanism to drive the incising blade forward for temporary exposure and rapid retraction of the blade.

Another object of the present invention is to provide a trocar which permits ambidextrous use since the trigger operating mechanism may be located on either side of the cannula housing.

A further object of the present invention is the provision of a trocar which can be manufactured as a single use disposal product or as a reusable product or a combination thereof.

Another object of the present invention is to provide a trocar which consists of multiple components which can be configured in various modules to minimize cost.

A still further object is to provide a trocar which can be used with the universal dynamic seal cannula of the present invention or alternately with other cannula structures.

Still another object is the provision of a trocar which can be used to introduce more than one cannula of the same size into the same patient to reduce cost.

A still further object is the provision of a cannula for use with a trocar having a dynamic seal which allows passage of all common surgical instruments of various diameters and which closes snugly around the circular shaft of the instrument to maintain an airtight seal.

Another object is the provision of a cannula with a seal using rotating multi-diameter sealing members positioned across the center of the cannula channel having graduations at standard instrument diameters.

Another object is the provision of a cannula housing which allows a lever connected to the linkage operating mechanism to extend outside the housing as a release button for opening the seal by hand.

Still another object is the provision of a cannula housing which may incorporate an incision port to accommodate flow of gasses or fluids into or out of the cannula.

A final object is the provision of a trocar and cannula combination which may consist of a rigid curve trocar and cannula sleeve or a curved rigid trocar and flexible cannula or a flexible trocar and a curved rigid cannula sleeve.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a perspective view of the incising trocar of the present invention.

FIG. 2 is an exploded perspective view of the trocar of FIG. 1.

FIGS. 3, 4, 5 and 6 are partial sectional views showing the operation of the blade drive mechanism of the present invention.

FIGS. 7, 8 and 9 are partial sectional views of the air seal arrangement of the invention.

DESCRIPTION OF THE PREFERRED EMBODIMENTS

The detailed embodiments of the present invention are disclosed herein, however, it is to be understood that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

Referring to the drawings, the figures illustrate a surgical trocar 10 and cannula 12 combination in accordance with the present invention. The trocar 10 includes safety mechanisms which limit the penetration of the incising blade into a body cavity and a cannula 12 which provides an air tight seal as the surgeon passes surgical instruments through the cannula for the purpose of operating on a patient. The trocar's 10 function is to create a passageway through a body wall in order that a surgeon may gain access to the interior cavity of the body by penetrating tissue and muscle. The trocar 10 is an elongated instrument having a distal end 14 which is used to incise a patient's tissue and a proximal end 16 which is used by a surgeon to manipulate and control the instrument. The distal end includes a scalpel type incising blade 18 which minimizes the amount of force necessary to penetrate the body while providing the surgeon tactile feedback and control over the insertion. The incising blade 18 is coupled directly to a blade drive shaft 20 at the distal end of the trocar by a connector 21 and suitable fasteners 22 in a manner known in the art. The blade drive shaft 20 extends to the proximal end 16 and communicates directly with a drive mechanism described in detail hereinbelow, to convert light finger pressure by the surgeon on a trigger 24 into a forward motion of the drive shaft 20 in blade 18.

The proximal end of the trocar/cannula combination is formed with a trocar housing 26 for easy handling and manipulation by the surgeon. The trocar housing 26 is complementary to a cannula housing 50 and together forms the enclosure for the drive mechanism and instrument seal. The trigger 24 lies in a direction parallel to the drive shaft 20 on an outer surface of the trocar housing 26 and the cannula housing 50 for easy access by the surgeon. The trigger 24 is mounted within a slot 31 formed in the housing 26 and is biased by a spring 33 to an inactive position. A spring guide 34 is cylindrical in shape and includes a tapered well 35 having an opening 29 formed in an upper flange member 37. The opening 29 includes an inner shoulder 39 which cooperates with the blade drive shaft 20 described hereinbelow. The trigger 24 includes a finger 32 which is structured to engage a spring guide 34 as shown in FIG. 3. A drive spring 36 is positioned within the housing 26 and sits above the spring guide 34 on the annular flange 37. In the unarmed position shown in FIG. 3, the drive spring 36 is relaxed and the spring guide 34 rests on a bottom shelf 38 of the housing 26.

The blade drive shaft 20 is positioned concentrically within a primary shaft 40 which in turn is positioned within a cannula sleeve 30 and extends the length of the instrument 2 between the proximal end 14 and the distal end 16. The end of the cannula sleeve 30 forms an obturator tip 42 at the distal end 14 of the instrument 2 which shields the blade 18 at all times except when the blade 18 is activated and projects beyond the edge of the tip 42 as described hereinbelow. The drive shaft 20 and the primary shaft 40 are telescopically removable from the tubular cannula sleeve 30 once an incision has been made by the surgeon leaving the sleeve 30 in place within a patient's body for insertion of suitable surgical instruments needed to perform the particular surgical procedure. The obturator tip 42 may be integrally formed with the instrument 2 or it may be interchangeable and disposable after each use.

Because a wide variety of different sized surgical instruments are used, the cannula 12 of the present invention includes structure to provide an airtight passageway into the surgical site which is accessible only because the cavity is distended by gas insufflation. For example, a surgeon may use the sleeve passage in the cannula housing 50 to insert an endoscope for viewing. Additional cannulae may be placed to allow passage of various other surgical instruments and for removal of tissue. The cannula 12 must keep the higher pressure gas on its distal side from leaking out when surgical instruments of various sizes are used in it. The present invention provides a cannula housing 50 which is supported on the instrument 2 between the trocar housing 26 and the cannula sleeve 30. The cannula housing 50 incorporates a universal dynamic seal 52 as shown in FIGS. 7, 8 and 9. The seal 52 is mounted within the cannula housing 50 and automatically adjusts to any diameter of the instrument being inserted through the cannula housing 50. The seal 52 also provides an absolute seal when no instrument is present. A release button 54 allows partial or full opening of the seal 52 to permit desufflation, that is venting of the inner cavity gasses, or removal of tissue. The seal 52 is formed of two parallel rotating multi-diameter seal members 56 mounted perpendicular to the longitudinal axis of the instrument 2 and across the shorter axis of the cannula housing 50. The seal members 56 are rotatably mounted within a dynamic seal housing 60 on a pair of pins 62 and are operably connected, in unison to a dynamic seal gear (not shown).

The dynamic seal members 56 include slotted curved face surfaces 64 which form an opening 66 which is progressively made larger or smaller depending upon the direction of rotation of the seal member 56. A spring 70 biases the seal members 56 to a normally closed position which creates a three millimeter hole centrally located between the members. A channel seal 72 is operably connected to the seal gear so that the channel opening is absolutely sealed when no surgical instrument is in the cannula 12. Preferably the seal members 56 are made of a single elastomer or combination of elastomers and low friction coatings to balance rigidity and compressibility.

The operation of the surgical trocar will be described with reference to FIGS. 3, 4, 5 and 6 in the drawings. The trocar is used within the cannula to insert it through a body wall. The obturator tip at the distal end extends past the end of the cannula sleeve. FIG. 3 illustrates the instrument in an inactivated position with the trigger 24 biased downwardly by spring 33. The drive spring 36 is relaxed in its expanded position and the spring guide 34 sits on the bottom shelf 38 with the upper portion of the drive shaft extending through the central opening 35 of the guide 34. Finger 32 rests against the lower edge of the annular flange 37 formed on the spring guide 34.

The surgeon presses the obturator tip against the outside surface of the body wall and pulls the trigger. When the trigger is actuated by a surgeon, it moves within the slot 31 in the housing 26. Finger 32 engages the underside of the annular flange 37 of the spring guide 34 raising it to a point above the end of the drive shaft 20. Drive spring 36 is compressed to its armed position. FIG. 5 illustrates the position of the actuating 20, elements when the trigger 24 is extended to its full extended position. Continued movement of the finger 32 causes the spring guide 34 to shift laterally until the finger 32 slips from under the edge of the flange 37. Once the finger 32 is released, the drive spring 36 expands downwardly with great force against the spring guide 34. Since the guide 34 is laterally shifted, the inner shoulder 39 of the opening 35 engages the end of the drive shaft 20 causing it to be propelled downwardly with great force as shown in FIG. 6 thereby exposing the blade 18 as it extends past the obturator tip 42. With the instrument placed against the tissue to be incised, the movement of the blade cuts the tissue before the tip and immediately returns to its inactive position in response to the action of return spring 41. After triggering the trocar, the surgeon presses it forward until resistance increases to a level where additional incising is required. The process may be continued by subsequent actuations of the trigger by the surgeon until a suitable incision is obtained. After the instrument cuts through the tissue, it is gently pushed downwardly to divide the body tissue until the instrument 2 penetrates into a body cavity. By pulling the trigger to incise and then pressing to divide tissue, the surgeon can separate the cutting operation from dividing tissue operation. This permits an incision/blunt dissection technique which minimizes trauma to the body wall during insertion. If he wishes, he may continually activate the trigger in order to incise while separating tissue. The cannular sleeve 30 then forms an opening to obtain access to the body cavity once the trocar portion of the instrument 2 is telescopically removed.

After penetrating the body wall, the trocar is removed and the cannula is left in place as a portal for surgical instruments. The portal must be kept closed in order to prevent the high pressure gas within the cavity from escaping into the room which would cause the abdomen to deflate and prevent further work until it is reinsufflated. The dynamic seal provides such a closure. Referring to FIGS. 7, 8 and 9, the structure of the dynamic seal assembly is shown. FIG. 7 shows the seal members 56 in a closed position. The channel seal 72 is rotated in place so that the three millimeter channel opening centrally located between the seal members is absolutely sealed. FIG. 8 illustrates a top view of the seal members in the closed position with the opening 66 centrally located between each member. FIG. 9 illustrates the seal members 56 in a fully open position which provides a ten millimeter opening therebetween. It will be appreciated that the size of the opening is limited by the action of a spring 70 which biases the seal members toward the closed position. With a surgical instrument or a similar device positioned within the cannula 12, it will be appreciated that the seal members are only able to close to the extent permitted by the size of the intervening instrument. Because of the shape of the slotted curved face surfaces 64, an air tight seal is provided around an instrument. Without an instrument in place, the release button may be actuated to permit venting of the cavity with the cannula in place. The seal members are also manually opened at such time as the surgeon may remove incised tissue through the cannula.

When there is no instrument in the cannula, the dynamic seal members are closed which allows the channel seal to cover the small opening on the distal side of the seal members. When an instrument is inserted into the dynamic seal it forces the seal members open. Since both seal members are linked by way of the dynamic seal gear, they will open in unison even if only one seal member is contacted by the instrument. This linkage keeps a gradually enlarging orifice in an uniform circular shape as the seal member opens. The orifice diameter increases in steps which allows facets on the seal member surface to form openings equal to the most common instrument sizes. The facets allow a greater contact area against the instrument. If the surgeon wishes to remove a tissue specimen which is larger than the diameter of the instrument, he may move the seal opening button parallel to the surface of the housing and open the dynamic seal members fully. In order to maintain sufficient pressure against the instrument to prevent gas leakage, the surface of the dynamic seal members must balance rigidity, compressibility and friction resistance. This is accomplished by making the seal members from a single elastomer or combination of elastomers and low friction coatings.

While various preferred embodiments have been shown and described, it will be understood that there is no intent to limit the invention by such disclosure, but rather, is intended to cover all modifications and alternate constructions falling within the spirit and scope of the invention as defined in the appended claims.

I claim:

1. A combination incising trocar and cannula instrument for incising the walls of a body cavity and inserting the cannula through the walls into the cavity comprising:

a trocar including a trocar housing, an incising blade mechanism including an incising blade, a blade drive means positioned in said trocar housing for driving the blade through body tissue and a trigger for operating said blade drive means;

said blade drive means including a drive spring, an annular spring guide supporting said drive spring and having an annular driving surface and annular flange formed thereon;

a blade drive shaft having an end cooperating with said annular driving surface for driving said blade drive shaft;

said annular spring guide and said drive spring being centrally positioned within said trocar housing and concentric with said blade drive shaft;

said trigger including an actuating finger for engaging said annular flange of said annular spring guide for moving said annular spring guide to compress said drive spring when said trigger is actuated; whereby continued movement of said trigger disengages said actuating finger from said annular flange of said spring guide causing said spring to decompress and drive said driving surface of said spring guide against said end of said blade drive shaft propelling said incising blade forwardly to incise body tissue; and a cannula having a cannula housing in alignment with said trocar housing, a cylindrical sleeve with a central opening extending from the cannula housing for insertion into the body cavity, and a sealing assembly for creating a seal between said cannula and said trocar during an incising procedure and creating a seal in said cannula thereafter when the trocar is removed.

2. The instrument of claim 1 further including a blade return spring to return said incising blade to a non-operable, retracted position; and a trigger return spring to return said trigger to a non-operable position.

3. The instrument of claim 1 wherein said trocar further includes a cylindrical outer shaft which concentrically surrounds the blade drive shaft and which telescopically fits into the opening of the cannula cylindrical sleeve.

4. The instrument of claim 1 wherein the driving surface of said annular spring guide is an annular inner shoulder formed on an inner opening of the annular spring guide.

5. The instrument of claim 1 wherein said incising blade is a scalpel.

6. The instrument of claim 1 wherein said instrument further includes an obturator tip at its distal end which covers said blade when the blade is in a retracted position.

7. The instrument of claim 6 wherein said obturator tip is removable and disposable.

8. A combination incising trocar and cannula instrument for incising the walls of a body cavity and providing a passageway through the walls into the body cavity comprising:

a trocar having an incising blade mechanism including an incising blade, a blade drive means and a trigger for operating said blade drive means; and a cannula having a sealing assembly for creating a seal between said cannula and said trocar during an incising procedure and creating a seal in said cannula thereafter when the trocar is removed; said cannula including a cannula housing, said sealing assembly being located in the cannula housing and including a pair of rotatably movable seal members centrally disposed within said housing and having sealing faces providing a variable circular opening between the faces in accordance with the rotatable position of the members, said sealing faces structured to engage walls of surgical instruments inserted in said cannula forming a seal between said sealing faces and said instruments; and an auxiliary seal member for sealing the opening between the faces of said seal members when instruments are not present within said cannula.

9. The instrument of claims 8 wherein said sealing faces are further defined by slotted curved surfaces; and said sealing assembly further includes a spring drive means biasing said sealing faces toward a sealing position.

10. The instrument of claim 8 further including manual actuating means for manually opening said sealing faces and said auxiliary seal member to provide unobstructed access through said cannula to the body cavity.

* * * * *